United States Patent

Zehel et al.

[11] Patent Number: 5,251,611
[45] Date of Patent: Oct. 12, 1993

[54] METHOD AND APPARATUS FOR CONDUCTING EXPLORATORY PROCEDURES

[76] Inventors: Wendell E. Zehel, 553 Harrogate Rd., Pittsburgh, Pa. 15241; Dwight M. Baumann, 1235 Squirrel Hill Ave., Pittsburgh, Pa. 15217; William B. Brenner, 81 Chapel Ridge Pl., Pittsburgh, Pa. 15238

[21] Appl. No.: 696,803
[22] Filed: May 7, 1991
[51] Int. Cl.$^5$ ............................................. A61B 1/00
[52] U.S. Cl. .................................................. 128/4
[58] Field of Search ........................ 128/4; 604/95, 282

[56] References Cited

U.S. PATENT DOCUMENTS

| | | | |
|---|---|---|---|
| 3,060,972 | 10/1962 | Sheldon | 128/4 |
| 4,432,349 | 2/1984 | Oshiro | 128/4 |
| 4,630,649 | 12/1986 | Oku | 138/122 |
| 4,651,718 | 3/1987 | Collins et al. | 128/4 |
| 4,686,963 | 8/1987 | Cohen et al. | 128/4 |
| 4,796,607 | 1/1989 | Allred, III et al. | 128/4 |
| 4,890,602 | 1/1990 | Hake | 128/4 |
| 4,969,709 | 11/1990 | Sogawa et al. | 350/96.26 |
| 4,977,887 | 12/1990 | Gouda | 128/4 |

OTHER PUBLICATIONS

Hasson, "Technique of Open Laparoscopy" (May 1979).
McKernan, "History: Laparoscopic General Surgery".

Primary Examiner—John J. Wilson
Assistant Examiner—Cindy A. Cherichetti
Attorney, Agent, or Firm—Walter J. Blenko, Jr.

[57] ABSTRACT

A method and apparatus for conducting exploratory procedures is disclosed. The apparatus includes a flexible steerable device which may alternately be stiffened along its entire length or a portion thereof and relaxed in order to effect movement of the device through a subject, such as the gut of a patient. The apparatus preferably comprises a pair of concentric conduits and is used by inserting the device into the subject, at least one of the concentric conduits being stiffenable. One of the conduits may be stiffened, acting as a guide for the other conduit. One conduit may be made flexible to be steered into the subject or follow the path prescribed by the other conduit or the path of least resistance. The device this minimizes the force exerted on the walls of the gut or other containment.

16 Claims, 5 Drawing Sheets

METHOD AND APPARATUS FOR CONDUCTING EXPLORATORY PROCEDURES

FIELD OF THE INVENTION

The present invention relates to methods and apparatus for conducting exploratory procedures on a subject, and more particularly to flexible devices having fiberoptic capability which may be guided to a point of interest within the human body.

BACKGROUND OF THE INVENTION

Instruments for examination and therapy of the esophagus and colon, or "endoscopes," as well as those used for abdominal, chest and intracranial procedures, such as "laparoscopes" typically employ a passage in a flexible hose or conduit which is inserted into the patient from the mouth or anus or surgically prepared opening. The distal end of the endoscope or laparoscope can be steered or pointed by means of manual controls mounted at the proximal end of the instrument. Typically, the first few inches of the distal end can be flexed 90° or more in any direction with respect to the body of the device by pulling on one or more cables running inside the instrument. Typically, a set of hand-operated knobs actuating a rack and pinion drive cause the desired cable or cables to be pulled, resulting in curvature of the distal end of the instrument. By this means, viewing devices connected to the distal end of the instrument, be they fiberoptic or miniature television, can be pointed toward point of interest, and the forward motion of the device can be approximately directed as the instrument is pushed into the patient. In addition, the trained endoscopist can employ the flexed distal end to temporarily distort the natural curve of the gut, typically in colonoscopy at the sigmoid, by hooking the instrument over a curve in the gut wall and pulling on it. This maneuver tends to straighten the gut so that further insertion of the endoscope is possible.

Present endoscopic and laparoscopic instruments offer limited working length, require great skill, encounter difficulty in maneuvering, and produce high internal forces against tissues. Moving the devices around a bend exerts a force on the tissues at that bend, and the strength of the tissue thus limits advancing the instrument around compound bends. Present instruments for urethral and laparoscopic applications, in particular, have little or no flexibility. Due to the stiffness of the present generation proctoscopes, manual controls do not provide adequate "feel" of the environment at the tip of the scope to the user. Such devices are thus steered by visual rules only, when a combination of visualization and tactile sensing could provide enhanced utility.

Throughout the maneuvers of the endoscope or laparoscope the gut or other distortable or distendable walls through which the device is being inserted often tend to resist movement and slip over the instrument, suddenly leaving the working end of any optical devices in a viewing position that is quite different from that which was observed just previously. Additionally, these semi-flexible instruments are used to guide specimen sampling devices to specific locations for tissue or sample retrieval.

Another common endoscopic procedure for which such instruments are used includes cauterization and polyp removal. In the case where a sample specimen is being gathered or where a snare is being used to catch and remove a polyp, the uncertainty of the location of the end of the scope and the surrounding walls of the gut creates a situation in which the operator of the device must engage in active and often protracted pursuit of the target. While this procedure is taking place, air or saline is typically injected to distend the gut to allow visibility of the target and surrounding tissue. Thus, along with the need to control air, saline, and tracking of moving targets in a breathing, flexing environment, endoscopic and laparoscopic procedures frequently require more than two hands, making an additional assistant necessary. In some instances this additional assistant may also be provided with a viewing port or in the case of the TV display may be watching the same screen as the endoscopist and laparoscopist.

Endoscopes apply pressure to the walls of the gut, especially when inserted to lengths of 50 cm or more, since some portion of the instrument will be following a relatively sharp curve around an angle of at least 90 degrees. In these conditions, any forward or backward motion of the endoscope will necessarily cause pressure to be exerted on the gut walls at these points. This tendency is compounded by the necessity to build instruments which are stiff enough to avoid buckling/bending when inserted against resisting forces in the gut. The gut often reacts to the presence of an endoscope by contracting radially, constricting its passage. The use of endoscopes in the gut is further impeded by the necessity of passing through the narrow portion of the sigmoid and several curves totalling more than 540 degrees. Attempts at forward (or backward) motions of the endoscope can result in relatively large and potentially dangerous forces being applied to the walls of the gut at its points of contact with the conduit. It has been noted that even the best endoscopists cannot always reach the cecum (end of the large intestine at the appendix) due to cramping of the gut, the inability to control the position of the endoscope along its entire length, and the danger of applying forces which might herniate or rupture the gut. The problem is further compounded by the fact that frequently the gut being inspected endoscopically is more fragile than a healthy gut, and thus least able to withstand the trauma of intrusive endoscopic procedures.

There is a real need in the art of endoscopic examination for a more flexible instrument that can avoid all or most of the above-described problems, yet still achieve the objectives of safe, reliable and efficient exploratory procedures.

It would be useful to provide an exploratory device which could be advanced through the gut, esophagus, surgically prepared opening or other cavity having compressible walls, without exerting undue force on these walls at any point, yet maintaining an effective degree of flexural control.

It would also be useful to provide an exploratory device which would be capable of reacting to motions occurring in the walls of the cavity being studied, such as a moving, living gut, by offering little resistance to such motions.

Furthermore, an advance in the art could be realized if there existed an exploratory instrument which, though flexible, could be stiffened along its entire length, providing a stable platform for the deployment of exploratory instruments, such as medical devices for performing visual or therapeutic procedures in, for example, laparoscope, urethral and proctological applications.

It would be useful, in addition, to provide an exploratory instrument which could be maintained in a relatively motionless position with respect to a target point on the wall of a moving subject, such as the gut.

SUMMARY OF THE INVENTION

The presently preferred embodiment of the invention comprises a flexible steerable device having a stiffening means, for use in exploratory procedures. The flexible device has a distal end which initiates the exploratory procedure and a proximal end which is operated by the physician or person performing the procedure. The device is capable of becoming rigid along its entire length when a stiffening actuator, operated at the proximal end of the device, is actuated.

In a preferred embodiment of the invention, an inner flexible conduit is slidably and concentrically engaged within an outer flexible conduit. Either or both the inner and outer conduit may be made rigid along its entire length by a stiffening device. In a most preferred embodiment of the invention, both the inner and outer conduit are stiffenable by a stiffening device. The stiffening device preferably comprises a series of segments, aligned with one another and strung on flexible cables which lock the segments together when the cables are pulled taut. The stiffening mechanism of the inner conduit may be an integral unit comprising an endoscopic device and a stiffenable hollow conduit combined within the same protective sheath or coating.

In a preferred method of practicing the invention, the flexible device is fed into a cavity of the subject being examined by alternately relaxing, sliding, and stiffening the inner and outer conduit with respect to each other while directing the distal end of the device toward the target point of interest. After the desired procedures are performed on the target point of the subject, the device is removed by alternately pulling the inner and outer conduit out in similar relaxing/sliding/stiffening sequence.

BRIEF DESCRIPTION OF THE DRAWINGS

The following are by way of example only, illustrations of preferred embodiments of the invention, wherein.

DETAILED DESCRIPTION OF PREFERRED EMBODIMENTS

Figure 1:
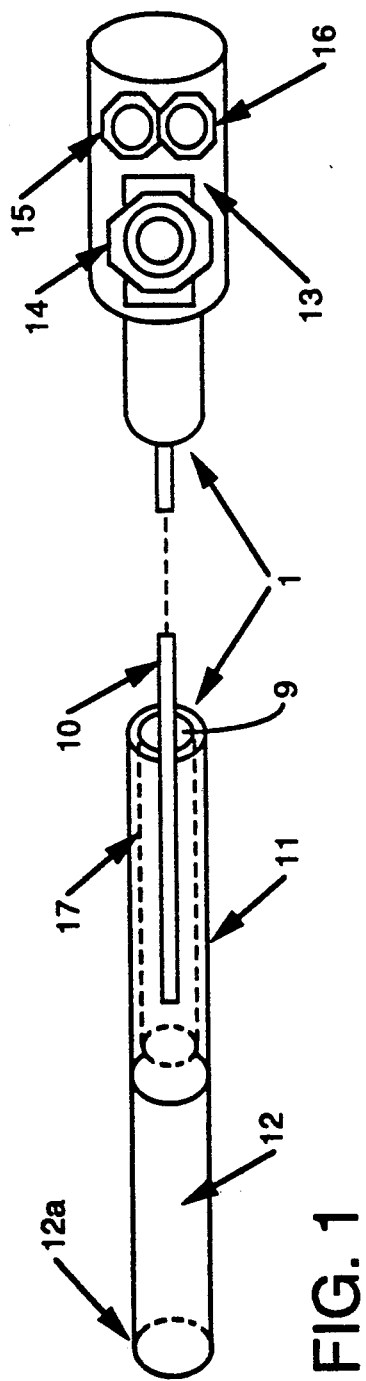
FIG. 1 is a partial cutaway view of a preferred embodiment of the invention.

Referring to FIG. 1, a preferred embodiment of the invention, a flexible steerable exploratory device, generally 1 is shown, which includes an inner flexible conduit, generally 10, which may be made rigid along its entire length, and shall be described in greater detail subsequently. The conduit 10 is threaded through an outer flexible conduit or similar tube 11, which, when relaxed, is sufficiently flexible to yield to forces within the gut or other cavity through which the device is inserted. Suitable materials of construction for this conduit include, by way of example, but not limitation, NEOPRENE, natural rubber, plastic, stainless steel, etc. The conduit preferably has an outside diameter suitable for use in the human gut, although other diameters could be employed depending on the end use and the stiffness of material of construction of the conduit 11.

The device 1 as illustrated in FIG. 1 has a distal end, generally 12, which is preferably flexible with respect to the flexible conduit 11 and may house an instrument port 12a for harvesting tissue samples and/or a vision aperture for relaying video transmissions, for example. As the device preferably has fiber-optic capability, fiber-optic fibers may be run through the flexible conduit 11. Other possible uses of the distal end 12 of the device 1 include containment of surgical cutting tools, lasers, vascular catheters, angioscopes, illuminating devices, clip and ligature devices and ultra-sound and dissecting devices and the like.

The flexible device 1 also has a proximal end, generally 13, which preferably contains a controller 14 for manipulating and steering the flexible distal end 12. The proximal end 13 also preferably contains a conduit advance/retreat controller, generally 15 and a conduit stiffen/relax controller, generally 16.

The controllers 14-16 may be commercially-available servo-motor driven, and/or pneumatically or hydraulically operated controllers. It is additionally possible to equip the controllers 14-16 with voice activation. Thus, the device 1 and in particular the distal end 12 thereof is a "smart" instrument, in that it may be guided by a joy stick, voice activation, "lock-on device," or laser or infra-red guidance system. A video screen may also be used to assist in guiding the device.

As illustrated in FIG. 1, the flexible exploratory device 1 includes within the outer flexible conduit 11 a passageway 17 through which the inner flexible conduit 10 is slidably disposed and free to travel. The relative size of the passageway 17 and conduit 10 is not critical, provided there is sufficient space to allow the inner conduit 10 and outer conduit 11 to slide relative to one another, yet not so much space as to permit the relaxed inner conduit 10 to buckle or bend appreciably when slid through the outer conduit 11.

The operation of the apparatus of FIGS. 1-8 facilitates the insertion of an exploratory device as follows by way of example:

(a) The inner flexible conduit system 10 is advanced within the outer flexible conduit 11, made rigid by the stiffen/relax control 16, and the distal end 12 of the exploratory device 1 is inserted into the gut or other cavity of the subject up to the first substantial curve or point of substantial resistance by the subject on the device 1.

(b) The distal end 12 is flexed using the control apparatus 14 to observe and determine the appropriate forward direction for the device, the distal end 12 is pointed in that direction, and the outer conduit is inserted, maintaining the inner flexible conduit system 10 in the rigid state. Thus, the inner flexible conduit 10 is maintained relatively axially stationary with respect to the subject's gut. The forward insertion of the outer conduit 11 continues until the flexible conduit 11 experiences appreciable resistance from the subject. The relatively short forward motion of the outer flexible conduit 11 while supported by the rigid inner conduit 10 precludes buckling/bending of that section of the outer conduit 11 unsupported by the inner conduit 10.

(c) The outer flexible conduit 11 is stiffened, the inner conduit 10 is then relaxed and, using the stiffened outer flexible conduit 11 as a guide, inner conduit 10 is advanced while the outer conduit 11 remains axially stationary with respect to the gut. When the inner conduit 10 is relaxed, the outer conduit 11 assumes the shape of the gut since neither the outer flexible conduit 11 nor the relaxed inner flexible conduit 10 offers appreciable resistance to the gut's movements or shape. The inner conduit 10 is again stiffened, for example, after reaching the distal end 12 of the flexible device.

The above procedure (steps b and c) is repeated cyclically, as necessary, until the distal end 12 of the flexible device 1 reaches the target point of the subject, at which time a predetermined procedure may be conducted on the target point. Although the above sequence of sliding, stiffening, relaxing of the inner flexible conduit and outer flexible conduit with respect to one another is a preferred method of practicing the invention, other combinations of sliding, stiffening and relaxing are possible using the invention.

Other methods and apparatus are possible in accordance with this invention. For example, it would be possible to use a flexible device in which the outer flexible conduit is not stiffenable, but the inner flexible conduit is stiffenable, or vice versa. Additionally, in those cases in which both the outer flexible conduit and inner flexible conduit are stiffenable, any sequence of stiffening, relaxing, advancing of one with respect to the other may be possible, and the particular sequence employed may depend upon the particular situation encountered.

The flexible device of the present invention, and particularly the distal end thereof, may be optionally fitted with a wide variety of instruments for conducting a wide variety of exploratory, surgical or other procedures. For example, the device may be fitted with retractors to assist in retracting tissue away from the point of interest, ultrasonic devices, which for example, may be used in exploratory procedures, irrigation/suction devices for use in surgical procedures, tissue clipping devices, voice activated directional equipment, lock-on devices and the like.

The procedures which may be conducted at the target point of the subject, once reached by the distal end of the flexible device, are likewise varied, and include, without limitation, visual inspection, polyp removal, biopsy, general surgery, photography, angioplasty, laser surgery and the like.

The apparatus and method of the invention may also be used in performing endoscopic and laparoscopic procedures, such as surgery, within the abdominal cavity. This may be accomplished, for example, by inserting the device through a surgically prepared opening in the abdomen and directing the distal end of the device to the target as described previously, using the ability of the device to alternately flex, relax and advance to maneuver around organs, arteries, etc , within the abdominal cavity. In this way, procedures such as appendectomies and gall bladder removal can be conducted using the apparatus and method of the invention, allowing such procedures to be performed on an out-patient basis.

When the inner conduit 10 is stiffened the distal end 12 of the endoscope is supported positionally such that movement of the gut along the body of the conduit is resisted. This support provides the stable platform needed for visual or therapeutic procedures in the gut or other cavity. Such stability is made possible by the unique stiffenable conduit of the invention, which imparts rigidity to the otherwise flexible conduit 11 along its entire length.

Removal of a conventional endoscope can cause trauma since a gut wall segment cramped about the instrument resists removal and thus causes stress at the curves of the gut along the length of the conduit, even if the conduit is otherwise very limp. Thus, the stiffenable conduit serves as a guide for endoscope removal by the following two-step procedure; repeated cyclically as needed.

(d) The inner conduit 10 is relaxed and partially withdrawn through the flexible conduit 11.

(e) The inner conduit 10 is stiffened, taking the shape of the gut, and the flexible outer conduit 11 is withdrawn. Thus, the inner conduit remains relatively stationary with respect to the gut (and the patient) as the flexible conduit 11 is removed.

In still another preferred embodiment of the invention the outer flexible conduit 11 may itself be made rigid along its entire length.

There are numerous embodiments of the controllable conduit apparatus of the present invention, examples of which are described below.

Figure 2:
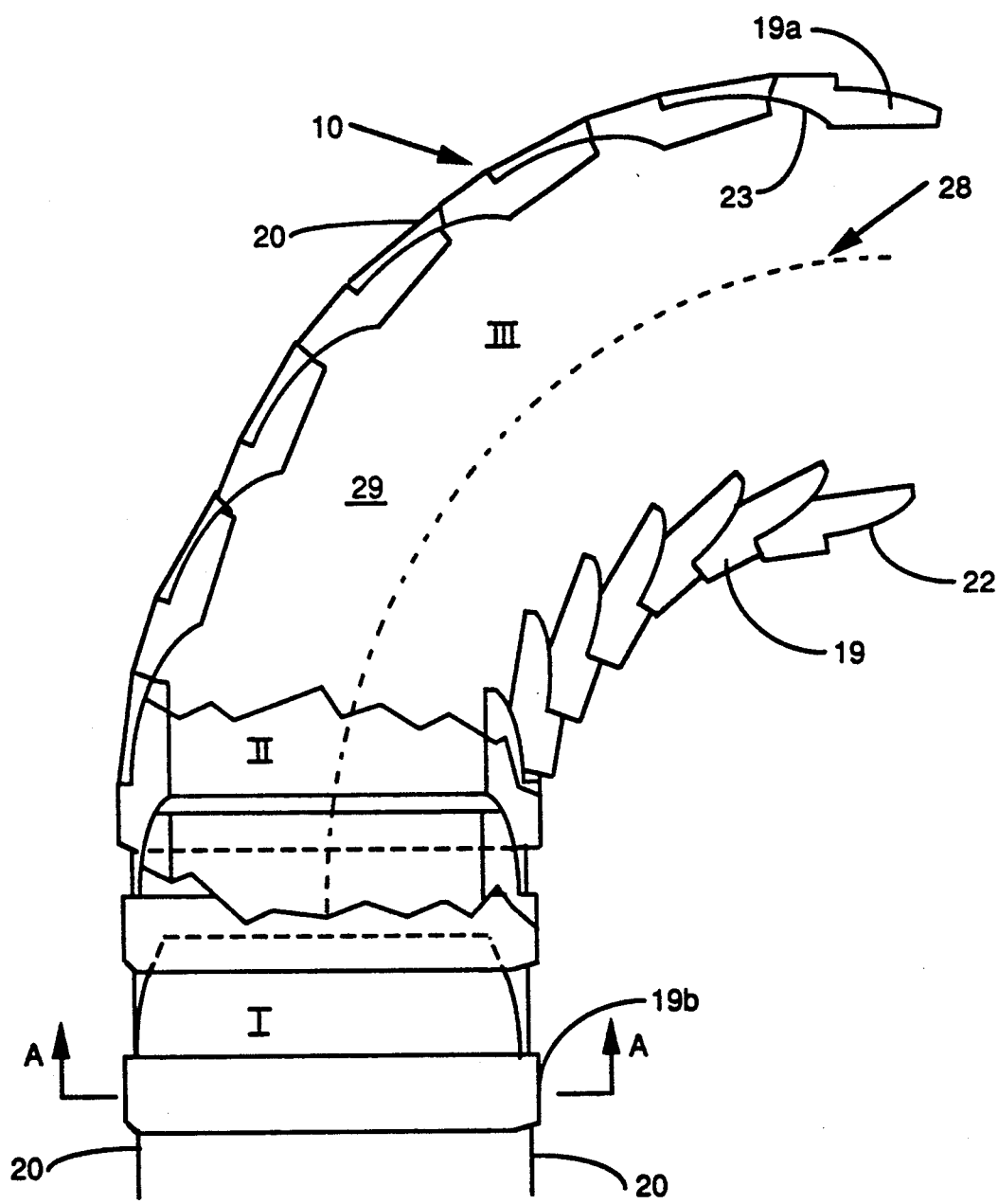
FIG. 2 is a partial breakaway transverse view of a schematic representation of a preferred embodiment of the invention.
Figure 3:
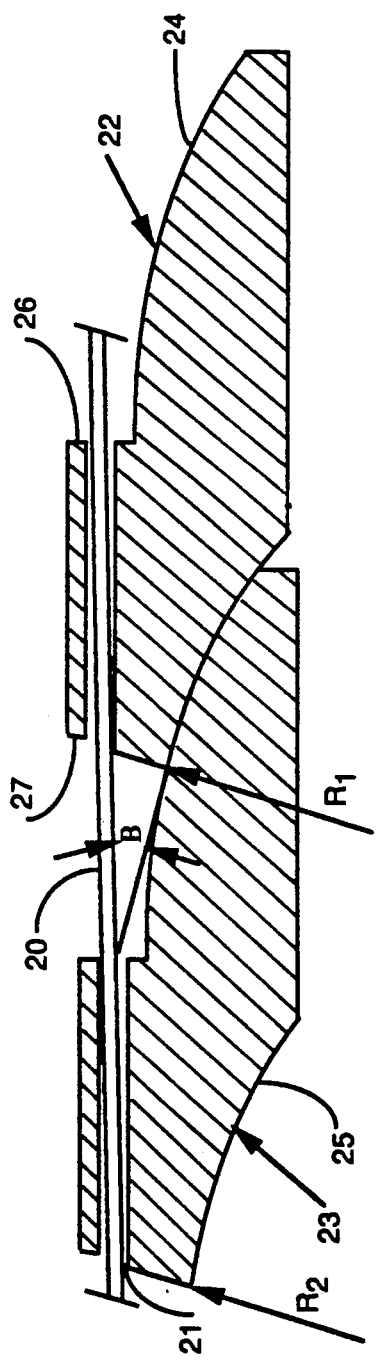
FIG. 3 is an enlarged cross-sectional view of an axially symmetric portion of two of the segments of the preferred embodiment of the invention illustrated in FIG. 2.

FIG. 2 illustrates a preferred inner flexible conduit 10 consisting of a plurality of generally cylindrically shaped beads or segments 19 strung on flexible cables 20 passing slidably through the segments 19 by way of a channel 21 bored therein, as best seen in FIG. 3. Alternatively, the cables 20 may be slidably disposed within the segments 19 by means of loops, grooves, or any other means slidably retaining the cables 20 at their radial position with respect to the segment, whether the cable is relaxed or flexed.

Section I of the FIG. 2 embodiment, i.e., that portion up to the first breakaway line, illustrates the external view of the beads 19. Section II of FIG. 2, i.e., that portion between the two breakaway lines, illustrates the internal contours of the beads 19. Section III of FIG. 2, i.e., that portion beyond the second breakaway line, illustrates the orientation of the beads 19 when the conduit 10 is bent.

The distal segment 19a attaches to the cables 20, the proximal segment 19b is supported with respect to ground, and all other segments 19 are free to slide axially along the cables 20. Each segment in the FIG. 2 and 3 embodiment is identically shaped, having a male end, in this case shaped like a spherical portion 22 and a female end, in this case comprising a spherical portion 23 carved out of the segment 19. The male portion 22 and female portion 23 nest within each other such that when the cables 20 are relaxed, the male end 22 of one segment 19 pivotally engages the female end 23 of the adjacent segment 19, and such that applying tension to the cables 20 causes friction forces between the spherical surfaces 24 and 25 of the male end 22 and female end 23, respectively, rendering the segments 19 immovable with respect to each other and rendering the inner flexible conduit 10 rigid along its entire length, $19b$–$19a$. In the preferred embodiment of FIGS. 2–3, both spherical surfaces 24 and 25 have the same radius $R_1$ and $R_2$ respectively, although this is not strictly required. Having slightly different radii $R_1$ and $R_2$ would more nearly approximate a line contact between the surfaces 24 and 25 and would tend to alter friction locking characteristics of the conduit 10.

As seen in FIGS. 2 and 3, each segment 19 preferably has a front stop means 26 and a back stop means 27 which limit the degree of bend of the conduit 10, preventing the segments 19 from being pulled apart or rotated beyond their maximum desired arc. The front and back stop means 26 and 27 are defined by a flange 30, which maintains the cable 20 a slight distance from the surface 24, such that the cable 20 stays close to the conduit when it follows the inside of a bend in the conduit. Alternatively the cable 20 may pass through loops on the inside of the conduit and follow an outside bend.

It is highly preferred that a plurality of flexible cables 20 be used in association with the inner flexible conduit 10 of FIG. 2. Most preferably, at least three such cables 20 are employed. A plurality of cables 20 is desired in order to insure that the sum of the tensile forces created by the cables 20 lies substantially along the centroid of the inner flexible conduit 10, illustrated by the dotted line 28. As can be readily appreciated, such a summing of forces is not generally possible when only one cable 20 is employed, unless the cable is centrally disposed within the interior space 29 of the conduit 10. However, such arrangement would interfere with the placement and use of various functional devices within the interior space 29 as discussed herein.

Figure 4:
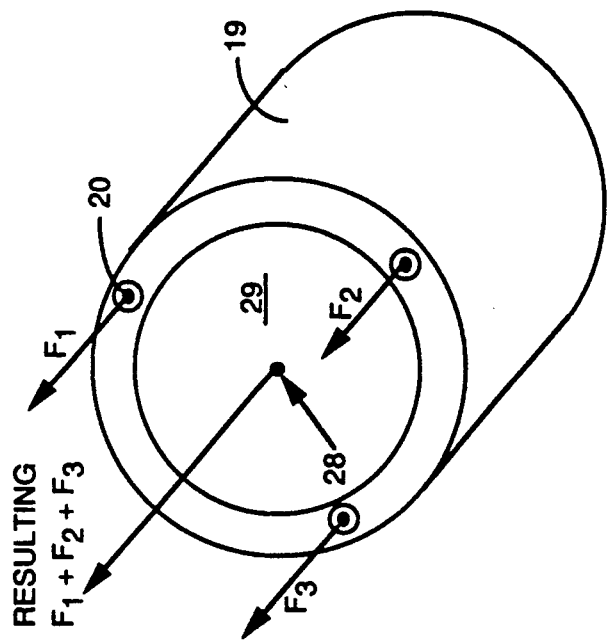
FIG. 4 is a schematic cross-sectional isometric view of the preferred embodiment of the invention illustrated in FIG. 2, (not to scale) taken along lines A—A.

When multiple flexible cables 20 are used, it is preferred that tensioning means be provided to achieve equal and simultaneous tension on all of the cables 20. Such means, which are known, include, by way of example, but not limitation, solenoid feedback systems, pulleys, and yokes to which all cables are connected. In one highly preferred embodiment of the invention the cables 20 are equally spaced around the perimeter of the segments 19 of the conduit 10, as illustrated in FIG. 4, in order to achieve the summing of the radial component of the applied forces $F_1$, $F_2$ and $F_3$ at the centroid 28 as previously discussed.

The segments 19 may be constructed of any suitable material, but preferably are sufficiently durable to withstand repeated use and resist abrasion. Examples of suitable materials include, by way of example, but not limitation, high impact plastic, shatterproof glass, stainless steel, composite carbon fiber, and ceramic or porcelain. The cables 20 may likewise be fabricated of any suitable material, preferably one which can withstand repeated tensing and relaxing, yet provide sufficient flexibility, such as stainless steel wire or nylon filament.

Figure 5:
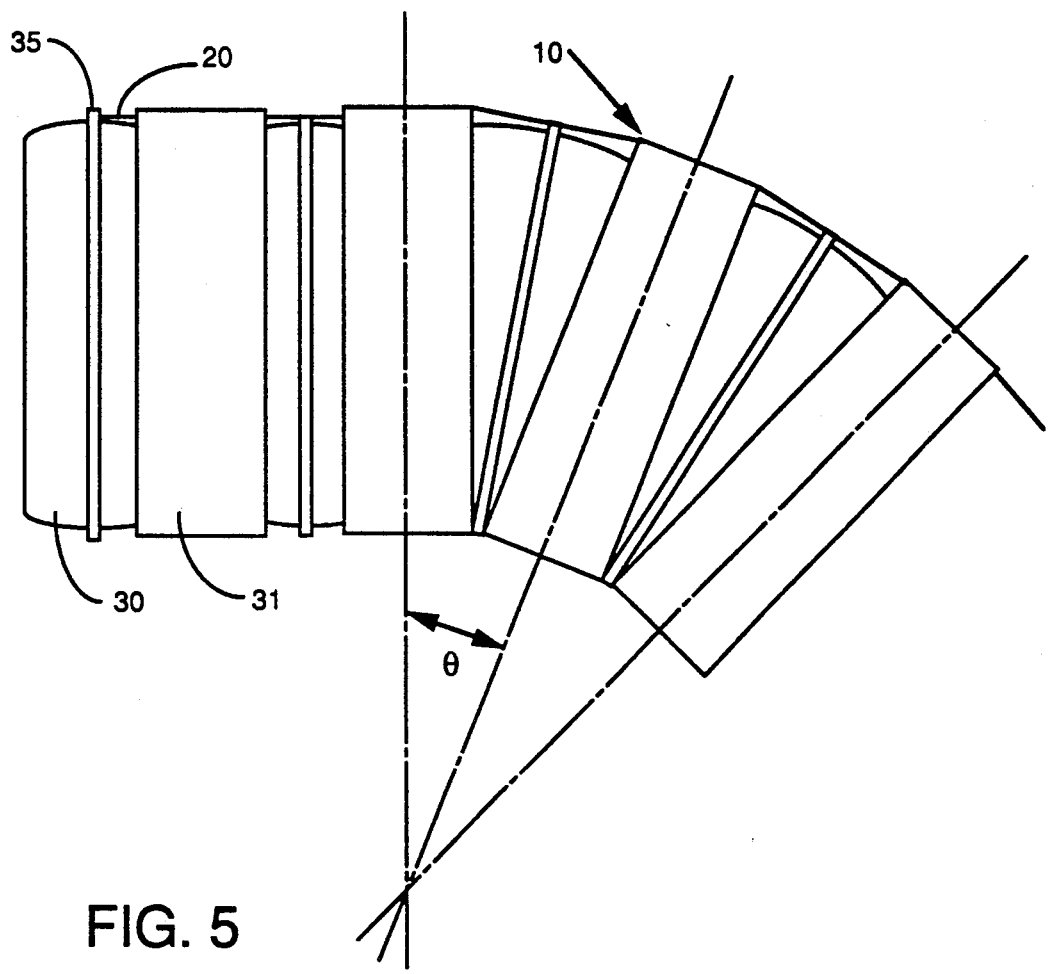
FIG. 5 is a schematic longitudinal view of a preferred embodiment of the invention.
Figure 6:
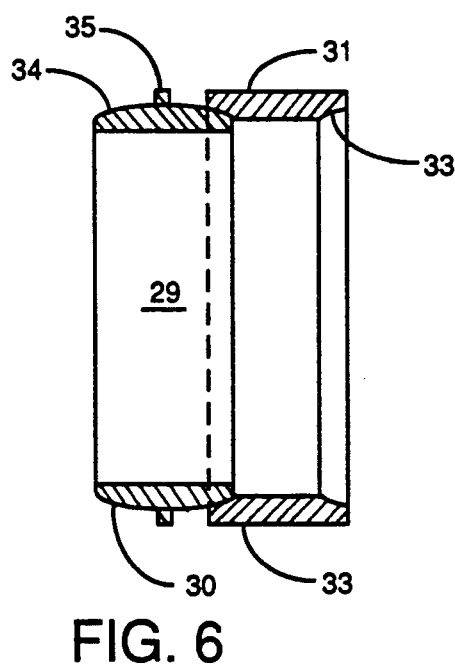
FIG. 6 is a cross-sectional view of a portion of the preferred embodiment of the invention illustrated in FIG. 5.

Another embodiment of a preferred inner flexible conduit 10, shown in FIGS. 5 and 6, consists of an alternating sequence of substantially spherical and cylindrical beads or segments 30 and 31, respectively, strung on at least one, preferably two, and most preferably three or more flexible cables 20. In the case in which the inner flexible conduit 10 has sufficient tensile strength it may also act as a central cable. As used herein, the term "substantially spherical" is intended to include segments 30 comprising only portions of spheres, as illustrated in FIGS. 5 and 6, as well as segments 30 which are virtually or completely spherical. The embodiment illustrated in FIGS. 5 and 6 functions substantially the same as that of FIGS. 2 and 4. The distal segment (not shown) is attached to the cable(s) 20 and the most proximal segment (also not shown) is supported with respect to ground.

In a preferred embodiment of the invention, the flexible conduit comprises spherical segments 30, each segment 30 having a cylindrical channel therein. The segments 30 may each have alternate male and female ends as in FIG. 2, which male and female ends mate in ball-and-socket fashion. The segments may alternatively be double-male and double-female ball-and-socket joints as illustrated in FIGS. 5 and 6.

When the cables 20 are actuated by pulling them taut, such as by the conduit stiffen/relax control 16 previously described, the segments 30 and 31 engage each other frictionally and lock into substantially the shape the conduit 10 had assumed immediately prior to actuation of the cables 20.

In the embodiment of FIGS. 5–6, the cylindrical segments 31 have at either end female portions or sockets having friction surfaces 33. These surfaces 33 may be rounded to accommodate the spherical segments 30, which act as a male coupling and have a friction surface 34 for frictionally engaging the friction surface 33 of the cylindrical segment 31. The spherical segments 30, as illustrated, preferably include a flange 35 forming a great circle about the spherical segments 30. Preferably, the cables 20 slidably pass through a hole in this flange 35, and also through a channel bored through the side wall 36 of the cylindrical segment 31.

As seen in FIG. 5, the flange 35 assists in limiting the maximum angle theta of bend associated with successive cylindrical segments 31. The conduit 10 of the FIGS. 5–6 embodiment has a hollow interior space 29 through which functional equipment, such as air lines, optical fibers and so on may pass. The pivotal geometries of each bead or segment 30 and 31 shown in FIGS. 5–6 are equivalent to the corresponding features of the single segment 19 of the conduit 10 of FIGS. 2–4. This approach of FIGS. 5–6 provides an alternate practical geometry using parts which are symmetrical both axially and end-for-end. Other geometries would be possible, such as segments having a conical female end and a spherical male end.

In a most preferred embodiment of the invention both the inner flexible conduit 10 and the outer flexible conduit 11 are hollow and stiffenable along their entire length. Referring to FIG. 1, the conduit 11 has slidably disposed within the annulus thereof, an inner flexible conduit 10 capable of being rendered rigid along its entire length as previously described, for example, by supplying tension to a set of cables 20 at its proximal end. The cables 20 pass through channels 21 in segments 19, 30, 31 as previously described. The outer conduit 11 may be fabricated the same as the inner flexible conduit 10, or may be one of the alternative embodiments herein described. In either case, the conduit 11 has a larger inside diameter than the inner flexible conduit's outside diameter, so as to accommodate the slidable disposition of the inner flexible conduit 10 therein.

In addition to providing sufficient space for the inner flexible conduit 10 to slide within the outer flexible conduit 11, the annular space 9 between the inner wall of the conduit 11 and the outer wall of the inner flexible conduit 10 preferably provides sufficient room for deployment of, for example, additional functional devices, such as electrical wiring, optical fibers and the like which may be used at the distal end 12 of the device. Alternatively, or additionally, such functional devices, wires and optical fibers, and the like, may be passed through the interior space 29 of the inner flexible conduit 10. Indeed, the cables 20 may comprise electrical wire or optical fibers.

Figure 7:
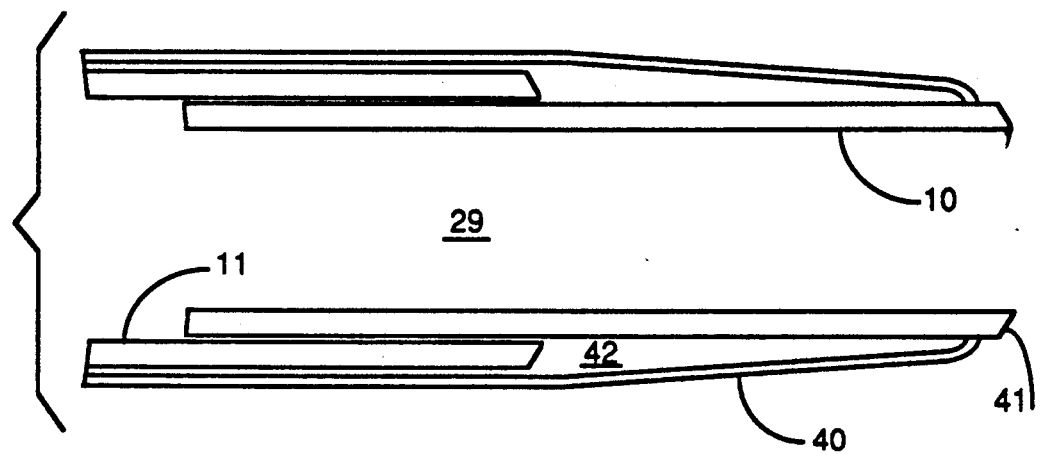
FIG. 7 is a schematic cross-sectional longitudinal view of a preferred embodiment of the invention.
Figure 8:
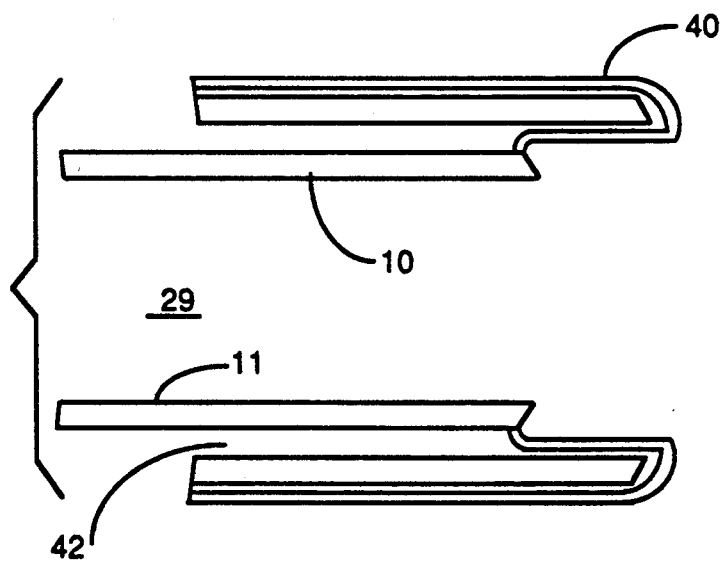
FIG. 8 is a schematic cross-sectional longitudinal view of a preferred embodiment of the invention.

Another preferred embodiment of the invention is illustrated schematically in FIGS. 7 and 8, which are longitudinal cross sections of an inner flexible conduit 10 slidably disposed within an outer flexible conduit 11, either or both of which may be stiffenable along its entire length, as previously described.

The embodiment of FIGS. 7 and 8 further comprises an elastic membrane 40, which encloses the outer flexible conduit 11 and extends to the distal end 41 of the inner flexible conduit 10, and is securely attached thereto, for example by adhesive means, clamping means or any other suitable fastening means that provides a substantially water-tight seal, preventing the ingress of blood, feces, or other fluids or undesirable matter in the space 42 between the membrane 40 and the outer surfaces of and space between the inner flexible conduit 10 and the outer flexible conduit 11.

As illustrated schematically in FIG. 7, the membrane 40 may be stretched taught when the inner flexible 10 advances relative to the outer flexible conduit 11. The membrane 40 is preferably attached at its other end to the outer wall of the outer flexible conduit, also in watertight manner, at any desired distance from the distal end of the outer flexible conduit 11.

The elastic nature of the membrane 40 assists in retracting the inner flexible conduit 10 relative to the outer flexible conduit 11 as illustrated schematically in FIG. 8. As shown, the membrane 40 has assumed a relaxed posture, yet is still able to prevent the ingress of undesirable material into the space 42.

The membrane 40 may be fabricated of any suitable material for the purpose, including, by way of example but not limitation, natural rubber, NEOPRENE ®, etc.

The central portion 29 of the endoscopic devices of the invention comprises a hollow interior space, or lumen, to be used for conveying air, gases, and/or saline and other solutions, and for containing actuator cables, optical fibers, electrical signal wires, as well as cauterizing and sampling devices, taking advantage of the fact that the neutral axis of the device does not change in length when the device is bent and/or distorted. Any useful endoscope, however, cannot have all such devices concentrated in a central location and design compromises must be made to allow some of the longitudinal members to be radially disposed from the center of the endoscope. Thus, such devices should be made of material that is longitudinally compressible or else the length changes must be accommodated in the end region of the endoscope.

Thus, a preferred embodiment of the invention is a concentric conduit that can be stiffened at will and that can itself be inserted into another concentric conduit, also stiffenable at will. This allows one conduit to be the track or guideway to allow the other conduit to advance either through or around it until the end of the advancing conduit extends past the stationary conduit and finds its equilibrium position or is steered by conventional endoscopic control methods to proceed for a shorter distance without the remainder of the system putting extra forces on the remainder of the gut or other tissue. Once the moving conduit is in its new location, it can be stiffened to become the guideway while the other conduit is relocated to the new position. In cases where the cumulative distortions and pressures of the endoscopic device have built up or where the device makes a full circle and passes near locations in which other passageways are being formed, there may be a need to relax both conduits simultaneously so as to allow the system to come to a new position and force equilibrium. In some cases the relaxation of one of the conduits may simply continue and the other conduit may proceed by being successively advanced and stiffened, then becoming the guideway for the more flaccid internal conduit, which may be progressively inserted without applying force to the gut at any position except for the small portion of its protruding, articulated end.

Because of the hollow, concentric nature of this preferred embodiment of the invention, standard endoscopic devices or, alternatively, the individual conduits, cables, wires etc., that are associated with standard endoscopic devices, thus can occupy the center section 29. The device thus can be an add-on device for an existing endoscope or the stiffening feature may be included in the basic endoscope and one or more segmented concentric devices of the invention may be used around the endoscope.

In either of the above cases or combination of cases, one of the primary advantages of the invention is the possibility of leaving a rigidized hollow conduit in place and withdrawing the centrally disposed members in order to insert other devices or to remove feces, sample tissue, or perform other surgical procedures within the region then accessible at the end of the fixed tubular emplacement.

In any of the embodiments, the desired effect is to have a self-centering connection which becomes rigid when the cables are taut and flexible when the cables are released. Small amounts of lubricants or foreign material between the joints may have significant effect on the ratio of stiffness to flexibility and thus surface finish can also additionally be chosen to alleviate some of the variability of unknown contaminants. Knurling surfaces for this kind of friction control is a known technique which may be used to add to the apparent friction coefficient, for example.

The most sensitive parameters in determining the ratio of stiffness to flexibility are the angle of the circular contact surface with respect to the tension cable, (friction angle), the tension in the cable, and the coefficient of friction. The hoop stress compliance of the two mating surfaces also enters into consideration for angles near the critical friction angle.

For some combinations of materials, planned or unplanned lubricants and geometries, there may also be provided additional mechanisms to insure flexibility on demand. These devices would include mechanisms for vibrating the joint or spring or other devices that separate the contacting members when the cables are released. The contacting angle, the working angle or range of rotation or the mating surfaces is also related to the size of the minimum and maximum openings in the concentric members in the stack. If the cables are dispersed around the annulus of the mating parts, at least three or more cables should be used. Each of the cables should be provided with a mechanism for applying a constant tension so that each cable has the same force, independent of its length. Devices for supplying equal force are well known and include sets of levers, pulleys, hydraulic or pneumatic cylinders supplied by a constant pressure source or by electromechanical means.

For safety considerations the ball or male end of a segment must not bind in the socket or female end of an adjacent segment unless tension is applied to the cables. It is therefore preferred that the mating surfaces are relatively frictionless until the load is applied to the cables. At a critical angle friction will oppose the release of the ball from the corresponding socket. For $\beta$ of FIG. 3 approaching zero degrees the male end responds as if it were being forced into a tapered conduit approaching a cylinder and binding would generally occur. The larger $\beta$ becomes the more flexible the segmented device but at the same time the area to accommodate the essential endoscopic components is reduced. Practical designs require consideration of the minimum 8 as a function of the coefficient of friction, which could be obtained experimentally by established engineering techniques.

In order to be assured that there is no net bending force between the segments in the longitudinal direction it is important that the net forces of the cables have their vector sum acting through or near the centroid of each spherical seat.

It will, of course, be appreciated by those skilled in the art that variations and other embodiments of the flexible stiffening devices would be possible and that the advantages of the invention may be realized with such alternate embodiments without departing from the spirit of the invention or the scope of the following claims.

Many other variations in the invention may likewise be practiced without departing from the spirit of the invention, which is not to be limited by the specific examples recited herein, rather is defined by the following claims. For example, although many of the examples detailed herein relate to use of the invention on a human subject in the gut, esophagus or surgical opening, it will be understood and appreciated by those skilled in the art that the utility of the invention and the advantages realized thereby are not limited to these exemplary uses. Uses of the invention in other parts of the human body, uses on non-human subjects, for example, on animals and within non-living subjects, such as cadavers, and uses for more general exploratory procedures, including through sections of pipe, conduit, earth excavations and the like could all be achieved by the invention and accordingly such varied uses are intended to fall within the scope of the following claims. Furthermore, while one preferred method of using the invention is through human manipulation, it is possible to manipulate the devices of the invention through robotic actuation and such uses are intended to be embraced within the scope of the following claims.

We claim:

1. A flexible steerable device for use in exploratory procedures, said device comprising an inner flexible conduit and an outer flexible conduit running substantially coaxially and concentrically over said inner flexible conduit, the inner flexible conduit and the outer flexible conduit being disposed for sliding axial movement relative to each other, said inner flexible conduit and said outer flexible conduit each having a distal end and a proximal end, at least one of said inner flexible conduit and said outer flexible conduit including stiffening means in operative connection therewith and operable to render the associated one of said inner flexible conduit and outer flexible conduit rigid along its length, and slidably axially movable relative to the other conduit whereby upon relative sliding movement, the conduit which is in a flexible state is constrained to follow the shape of the conduit which is in a rigid state.

2. The flexible steerable device of claim 1, both said inner flexible conduit and outer flexible conduit having a said stiffening means.

3. The flexible steerable device of claim 2 wherein each said stiffening means for at least one of said inner flexible conduit and said outer flexible conduit comprises a series of segments aligned with one another and strung on cable means, each said segment having a male end and/or a female end, said male end of each segment adapted to pivotally engage the female end of an adjacent segment when said cable means is relaxed, said male end adapted to frictionally engage said female end when said cable means is actuated.

4. The flexible steerable device of claim 3 wherein said outer flexible conduit includes a plurality of said stiffening means equally spaced about the walls of said conduit.

5. The flexible steerable device of claim 3 wherein said stiffening means comprise substantially spherical and substantially cylindrical segments aligned in alternating sequence.

6. The flexible steerable device of claim 3 wherein all of said segments of said stiffening means are substantially spherically shaped and each said stiffening means cable means passes through a channel within each said segment.

7. The flexible steerable device of claim 3 wherein said cable means for each said stiffening means is activated by pulling said cable taut at its proximal end, said cable being attached at its distal end to the most distal segment of said stiffening means relative to the proximal end thereof.

8. The flexible steerable device of claim 7 wherein each said cable means for each said stiffening means is activated by cable tensioning means connected to the proximal end of said cable means.

9. The flexible steerable device of claim 1 wherein said flexible steerable device is adapted for use in the human body and said flexible steerable device is provided at its distal end with means for conducting visual examination within said human body.

10. The flexible steerable device of claim 9 further including at said distal end means for conducting surgical procedures within said human body.

11. The flexible steerable device of claim 1 further comprising an elastic membrane enclosing at least a portion of said outer flexible conduit and said inner flexible conduit, said membrane being fastened at one end to said distal end of said inner flexible conduit and being fastened at its other end to the outer surface of said outer flexible conduit.

12. A method of conducting exploratory procedures on a subject with a flexible steerable device having a distal end, comprising the steps of:

a. inserting the distal end of said flexible steerable device through an opening in said subject, said flexible steerable device comprising an inner flexible conduit and an outer flexible conduit, said inner flexible conduit being slidably and concentrically positioned within said outer flexible conduit, at least one of said inner flexible conduit and outer flexible conduit capable of being made rigid along its entire length by a stiffening means;

b. stiffening at least one of said inner flexible conduit and said outer flexible conduit, thereby stiffening said flexible steerable device and directing the distal end of said stiffened flexible steerable device toward a target point within said subject until appreciable resistance from said subject is encountered by said flexible device;

c. directing the distal end of said flexible steerable device to said target point, by alternately sliding said outer flexible conduit over said inner flexible conduit and sliding said inner flexible conduit through said outer flexible conduit, and by alternately stiffening and relaxing at least one of said outer flexible conduit and said inner flexible conduit;

d. repeating step (c) as required, alternately sliding, stiffening and relaxing said inner flexible conduit and/or said outer flexible conduit until said flexible steerable device distal end reaches said target point.

13. The method of claim 12 including the additional step of e. performing a predetermined procedure on said subject with said distal end of said flexible steerable device at said target point.

14. The method of claim 13 including the additional steps of f. removing said flexible steerable device by alternately relaxing and stiffening either said inner flexible conduit or said outer flexible conduit and slidably removing a portion of one from the other, while retaining the other substantially stationary with respect to said subject;

g. repeating step (f) as required until said flexible steerable device is removed from said subject.

15. The method of claim 12 wherein the subject is a human body.

16. The method of claim 12 wherein said flexible steerable device further comprises at the distal end thereof means for conducting visual examination of said subject.

* * * * *